US006596402B2

(12) United States Patent
Soerens et al.

(10) Patent No.: US 6,596,402 B2
(45) Date of Patent: Jul. 22, 2003

(54) ABSORBENT, LUBRICIOUS COATING AND ARTICLES COATED THEREWITH

(75) Inventors: Dave Soerens, Roswell, GA (US); Sohail Malik, Roswell, GA (US); Cameron G. Rouns, South Jordan, UT (US); Sharon L. Greene, Canton, GA (US); Archel A. Ambrosio, San Diego, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 146 days.

(21) Appl. No.: 09/752,002

(22) Filed: Dec. 29, 2000

(65) Prior Publication Data

US 2002/0132540 A1 Sep. 19, 2002

(51) Int. Cl.$^7$ ................................ B32B 9/04

(52) U.S. Cl. ................ 428/447; 427/387; 442/99; 525/100; 525/105; 525/106

(58) Field of Search ................ 525/100, 104, 525/106; 428/447; 427/387; 442/99

(56) References Cited

U.S. PATENT DOCUMENTS

| | | | | |
|---|---|---|---|---|
| 3,959,242 A | * | 5/1976 | Watts et al. | 525/56 |
| 3,963,805 A | | 6/1976 | Chu | 260/874 |
| 4,593,071 A | | 6/1986 | Keogh | 525/288 |
| 4,753,993 A | | 6/1988 | Keogh | 525/100 |
| 4,767,820 A | | 8/1988 | Keogh | 525/72 |
| 4,806,594 A | | 2/1989 | Gross et al. | 525/64 |
| 5,047,476 A | | 9/1991 | Keogh | 525/106 |
| 5,112,919 A | | 5/1992 | Furrer et al. | 525/263 |
| 5,389,728 A | | 2/1995 | Prejean | 525/102 |
| 5,945,476 A | * | 8/1999 | Roesler et al. | 524/588 |
| 6,013,855 A | * | 1/2000 | McPherson et al. | 623/23.76 |
| 6,020,071 A | | 2/2000 | Watson | 428/423.1 |
| 6,054,523 A | | 4/2000 | Braun et al. | 524/503 |

FOREIGN PATENT DOCUMENTS

| | | | |
|---|---|---|---|
| EP | 0132910 A2 | 2/1985 | D06M/15/643 |
| EP | 0475664 B1 | 3/1992 | A61K/9/02 |
| EP | 0705861 B1 | 4/1996 | C08G/73/02 |
| EP | 0844265 A1 | 5/1998 | C08G/65/22 |
| EP | 0992252 A2 | 4/2000 | A61L/29/08 |
| EP | 1059320 A2 | 12/2000 | C08G/65/00 |

OTHER PUBLICATIONS

Article: London/HMSO; *British Pharmacopoeia 1993*; Addendum 1996; "Surgical Materials;" May 1, 1996; copyright 1995; 4 pages; see pp. 1943–1944.
Abstract: Keogh et al.; "Flame Retardant Compositions;" 5262467; filed Nov. 12, 1992; issued Nov. 16, 1993.
Abstract: Keogh et al.; "Flame Retardant Compositions;" 5211746; filed Jun. 22, 1992; issued May 18, 1993.

Abstract: Keogh; "Process for Crosslinking Hydrolyzable Copolymers;" 5047476; filed May 12, 1989 issued Sep. 10, 1991.
Abstract: Yang et al.; "Method for Manufacturing Vinylalkoxysilanes;" 5041595; filed Sep. 26, 1990; issued Aug. 20, 1991.
Abstract: Topcik; "Process for Extruding a Thermoplastic Copolymer;" 4873042; filed Mar. 25, 1988; issued Oct. 10, 1989.
Abstract: Topcik et al.; "Process of Producing Foamed Products;" 4867923; filed Dec. 21, 1984; issued Sep. 19, 1989.
Abstract: Gross et al.; "Water Curable Compositions of Silane containing ole36in Polymers;" 4806594; filed Jun. 17, 1987; issued Feb. 21, 1989.
Abstract: Topcik; "Elastomer Polyolefin Blends;" 4798864; filed Oct. 7, 1987, issued Jan. 17, 1989.
Abstract: Robeson; "Orthopedic/Orthotic Splint Materials;" 4784123; filed Jan. 3, 1986; issued Nov. 15, 1988.
Abstract: Keogh; "Compositions of a Relatively Water–stable Thermoplastic Polymer and Tetremethyl Titanate Dispersed in an Alkylene–Alkyl Acrylate Copolymer Matrix;" 4767820; filed Feb. 2, 1987; issued Aug. 30, 1988.
Abstract: Keogh; "Compositions Based on Thermoplastic Polymers and Metal Carboxylate Silanol Condensation Catalysts;" 4753993; filed Aug. 14, 1986; issued Jun. 28, 1988.
Abstract: Topcik; "Roofing Membranes;" 4722961; filed Jun. 16, 1986; issued Feb. 2, 1988.
Abstract: Keogh; "Composition Based on Water–Curable Thermoplastic Polymers and Metal Carboxylate Silanol Condensation Catalysts;" 4707520; filed Aug. 21, 1985; issued Nov. 17, 1987.
Abstract: Angell; "Molding Method Using Fast Curing Fiber Reinforced, Low Viscosity Thermosetting Resin;" 4692291; filed May 9, 1984; issued Sep. 8, 1987.
Abstract: Keogh et al.; "Compositions Based on Alkylene–Alkyl Acrylate Copolymers and Silanol Condensation Catalysts;" 4617338; filed Sep. 27, 1984; issued Oct. 14, 1986.
Abstract: Keogh et al.; "Scorch Resistant Compositions Based on Water—Curable Thermoplastic Polymers Having Hydrolyzable, Pendant Silane Moieties, and Organo Titanates;" 4598116; filed Nov. 9, 1984; issued Jul. 1, 1986.

(List continued on next page.)

*Primary Examiner*—Robert Dawson
*Assistant Examiner*—Christopher M. Keehan
(74) *Attorney, Agent, or Firm*—Nelson Mullins Riley & Scarborough, LLP

(57) ABSTRACT

Coatings are formed by applying to article a copolymer of a water soluble base polymer having graft polymerized thereto an organic moiety that includes a group that reacts with water to form a silanol group, and then curing the copolymer to form a crosslinked hydrogel coating that is absorbent, lubricious and substantially non-water soluble. Coating compositions, coated articles the subject coatings are also described.

33 Claims, No Drawings

OTHER PUBLICATIONS

Abstract: Keogh; "Relatively Water–Stable Compositions Based on Thermoplastic Polymers Containing Pendatn Silane Moieties;" 4593072; filed Nov. 9, 1984; issued Jun. 3, 1986.

Abstract: Keogh; "Water–Curable, Silane Modified Ehtylene Polymers;" 4593071; filed Nov. 9, 1984; issued Jun. 3, 1986.

Abstract: Keogh; "Composition of a Relatively Stable Polymer of an Olefinic Monomer and an Unsaturated Silane, and an Organo Titanate;" 4579913; filed Nov. 9, 1984; issued Apr. 1, 1986.

Abstract: Keogh; "Water–curable, Silane Modified Alkylene–Alkyl Acrylate Copolymers and a Process for the Production Thereof;" 4575535; filed Sep. 17, 1984; issued Mar. 11, 1986.

Abstract: Brown.; "Extruder Assembly for Extruding Water– Curable Silane Modified Polymers;" 4564349; filed Apr. 27, 1984.

Abstract: Keogh; "Polysiloxanes from Acyloxysilanes using Organo Metallic Catalyst;" 4552941; filed Nov. 5, 1982; issued Nov. 12, 1985.

Abstract: Barnabeo; "Water Curable, Azide Sulfonyl Silane Modified Ethylene Polymers;" 4551504; filed Jan. 18, 1984; issued Nov. 5, 1985.

Abstract: Keogh; "Production of Water–Curable, Silane Modified Thermoplastic Polymers;" 4526930; filed Sep. 23, 1983.

Abstract: Barnabeo; "Water–Curable, Azide Sulfonyl Silane Modified, Alkylene–alkyl Acrylate Copolymers;" 4514545; filed Jan. 18, 1984; issued Apr. 30, 1985.

Abstract: Rifi; "Water–Curable, Silane Modified Chlorosulfonated Olefinic Polymers and a Process for the Preparation thereof;" 4493924; filed Jun. 10, 1983; issued Jan. 15, 1985.

Abstract: Keogh et al.; Compositions Based on Alkylene–Alkyl Acrylate Copolymers and Silanol Condensation Catalysts; and the Use thereof in the Production of Covered wires and Cable 4489029; filed Jun. 1, 1983; issued Dec. 18, 1984.

Abstract: Keogh; "Compositions Based on a Polysiloxane and an Organo Titanate and the Use thereof in the Preparation of Water Curable, Silane Modified Alkylene–Alkyl Acrylate Copolymers;" 4446279; filed Feb. 23, 1983, issuedd May 1, 1984.

Abstract: Keogh; "Process of Producing a Water–Curable, Silane Modified Alkylene–Alkyl Acrylate Copolymer by Reacting an Alkylene–Alkyl Acylate Colpolymer with a Polysiloxane Predispersed in a Thermoplastic Resin Matrix;" 4440907; filed Sep. 17, 1982; issued Apr. 3, 1984.

Abstract: Turbett; "Compositions of Hydrocarbon–Substituted Diphenyl Amines and High Molecular Weight Polyethylene Glycols; and the Use Thereof as Water–tree Retardants for Polymers;" 4440671; filed Feb. 23, 1983, issued Apr. 3, 1984.

Abstract: Keogh; "Water–Curable, Silane Modified Alkyl Acrylate Copolymers and a Process for the Preparation Thereof;" 4434272; filed Feb. 22, 1982, issued Feb. 28, 1984.

Abstract: Barnabeo; "Polysiloxanes and the Use thereof in the Production of Silane Modified Alkylene–Alkyl Acrylate Copolymers;" 4408011; filed Sep. 13, 1982, issued Oct. 4, 1983.

Abstract: Keogh; "Masterbatch Composition Comprising a Matrix Having a Polysiloxane Dispersed Therein and a Method for the preparation Thereof;" 4369289; filed Aug. 20, 1981, issued Jan. 18, 1983.

Abstract: Keogh; "Compositions Based on Water–Curable, Silane Modified Copolymers of Alkylene–Alkyl Acrylates;" 4353997; filed Apr. 2, 1981, issued Oct. 12, 1982.

Abstract: Keogh; "Water–Curable, Amino Silane Modified Alkylene–Alkyl Acrylate Copolymers;" 4343917; filed Apr. 2, 1981, issued Aug. 10, 1982.

Abstract: Keogh; "Production of Silane Modified Copolymers of Alkylene–Alkyl Acrylates;" 4328323; filed Sep. 30, 1980, issued May 4, 1982.

Abstract: Keogh; "Water–Curable Silane Modified Alkylene Alkylacrylate Copolymer and a Process for its Production;" 4291136; filed Aug. 29, 1979, issued Sep. 22, 1981.

Abstract: Keogh et al.; "Flame Retardant Compositions;" EP0598344A1; filed Nov. 11, 1983, issued May 25, 1994.

Abstract: Keogh et al.; "Flame Retardant Compositions;" EP0575946A3; filed Jun. 21, 1993, issued May 18, 1994.

Abstract: Yang et al., "Method for Manufacturing Vinylalkoxysilanes;" EP0477894A1; filed Sep. 25, 1991, issued Apr. 1, 1992.

Abstract: Rifi.; "Thermoplastic Olefins;" EP0412518A3; filed Aug. 7, 1990, issued Apr. 22, 1992.

Abstract: Turbett et al.; "Tree Resistant Compositions;" EP0410431A1; filed Jul. 25, 1990, issued Jan. 30, 1991.

Abstract: Turbett et al.; "Tree Resistant Compositions;" EP0410431B1; filed Jul. 25, 1990, issued May 17, 1995.

Abstract: Keogh; "Process for Crosslinking Hydrolyzable Copolymers;" EP0401540A3; filed May 11, 1990, issued Mar. 11, 1992.

Abstract: Keogh; "Process for Crosslinking Hydrolyzable Copolymers;" EP0401540B1; filed May 11, 1990, issued Mar. 1, 1995.

Abstract: Turbett at al.; "Tree Resistant Compositions;" EP0341644A1; filed May 9, 1989, issued Nov. 15, 1989.

Abstract: Turbett et al.; "Stabilization of Crosslinked VLDPE;" EP0340785A3; filed May 5, 1989, issued Mar. 27, 1991.

Abstract: Rifi; "Hot Melt Adhesives;" EP0319043A3; filed Dec. 2, 1988, issued Mar. 20, 1991.

Abstract: Gross et al.; "Water Curable Compositions;" EP0295702A3; filed Jun. 16, 1988, issued Oct. 9, 1991.

Abstract: Gross et al.; "Water Curable Compositions;" EP0295702B1; filed Jun. 16, 1988, issued Oct. 12, 1994.

Abstract: Kondo Hirofumi; "Lubricant and Magnetic Recording Medium and Magnetic Head Lubricated Therewith;" EP09255979; filed Mar. 21, 1996, issued Sep. 30, 1997.

* cited by examiner

ABSORBENT, LUBRICIOUS COATING AND ARTICLES COATED THEREWITH

CROSS REFERENCE TO RELATED PATENTS AND PATENT APPLICATIONS

The subject matter of the present invention is related to copending and commonly assigned patent applications titled "Moisture-Induced Poly(Ethylene Oxide) Gel, Method Of Making Same And Articles Using Same", and "Modified Poly(Ethylene Oxide), Method Of Making Same And Articles Using Same", both of which were filed on May 26, 2000.

BACKGROUND OF THE INVENTION (1) Field of the Invention

The present invention relates to an absorbent, lubricious coating, and more particularly to an absorbent, lubricious coating which is water insoluble and is formed from a modified water soluble base polymer that crosslinks upon exposure to moisture.

(2) Description of the Related Art

Coatings that are water absorbent and lubricious are useful in medical applications such as coatings for surgical instruments, for in-dwelling biomaterials such as stents, screws and internal splints, and for tubing, catheters, wire guides and the like. Such coatings minimize the trauma of contact of the article with tissues and biological fluids. In particular, such coatings are particularly useful in fabrics and bandages that contact cuts and abrasions to provide coated fabrics and bandages that can absorb excess wound fluid without irritating exposed tissue.

Other products, such as disposable diapers, incontinence aids and feminine hygiene products are also great conveniences that depend upon characteristics of absorbency and biological inertness. However, these products are disposed of after a single use and most often ultimately are deposited into a landfill. If such products are made of non-biodegradable material, they persist in the landfill and can limit the later use of the landfill area while continuing to occupy space in the fill. Accordingly, it would be advantageous if the materials that comprise these disposable products were biodegradable.

Approaches that have been used in the past to provide materials that are lubricious and absorbent include the production of laminates having a porous non-stick surface backed by an absorbent pad, the synthesis of fibers and fabrics from absorbent, lubricious materials, and the formation of absorbent coatings on structurally durable, but non-absorbent materials. However, each type of structure has encountered its own particular problems. For example, laminates formed by bonding absorbent coatings to non-absorbent materials often delaminate or are impossible to bond together at all. Fibers and films produced from lubricious, absorbent compounds often have low strength and lack of integrity and durability.

Recent development efforts have provided materials that show promise for the types of uses described above and have improved processibility characteristics, and often, increased strength and durability. For example, in U.S. Pat. No. 6,054,523, Braun et al., describe materials that are formed from organopolysiloxanes containing groups that are capable of condensation, a condensation catalyst, an organopolysiloxane resin, a compound containing a basic nitrogen, and polyvinyl alcohol. The materials are reported to be suitable for use as hydrophobic coatings and for paints and sealing compositions.

Other workers have reported the production of graft copolymers having silane functional groups that permitted the initiation of cross-linking by exposure to moisture. Prejean (U.S. Pat. No. 5,389,728) described a melt-processible, moisture-curable graft copolymer that was the reaction product of ethylene, a 1–8 carbon alkyl acrylate or methacrylate, a glycidyl containing monomer such as glycidyl acrylate or methacrylate, onto which has been grafted N-tert-butylaminopropyl trimethoxysilane. The resulting copolymers were reported to be useful as adhesives and for wire and cable coatings, however, would not be expected that such materials would be either water-absorbent or lubricious when wet.

Furrer et al. (U.S. Pat. No. 5,112,919) reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane; and a free-radical generator, such as an organic peroxide; and heating the mixture. The copolymers could then be cross-linked by reaction in the presence of water and a catalyst, such as dibutyltin dilaurate, or stannous octoate.

Keough (U.S. Pat. No. 4,593,071) reported moisture cross-linkable ethylene copolymers having pendant silane acryloxy groups. The resultant cross-lined polymers were reported to be especially resistant to moisture and to be useful for extruded coatings around wires and cables. The same group has reported water similar moisture curable polymers involving silanes in U.S. Pat. Nos. 5,047,476, 4,767,820, 4,753,993, 4,579,913, 4,575,535, 4,551,504, 4,526,930, 4,493,924, 4,489,029, 4,446,279, 4,440,907, 4,434,272, 4,408,011, 4,369,289, 4,353,997, 4,343,917, 4,328,323, and 4,291,136. Since the cured products of these formulations are reported to be useful for coverings for wire and cable, and for non-conductive coatings for electrical conductors, it would be expected that they are durable coatings for which properties such as water absorbency and biodegradability would be a disadvantage.

Water-swellable polymers have reportedly been produced by cross-linking water soluble polymers, such as poly (ethylene oxide). It is known that poly(alkylene oxides), such as poly(ethylene oxide), can be cross-linked through gamma irradiation. Depending upon the degree of irradiation and the degree of cross-linking, the properties of the cross-linked polymer can range from a water soluble material to a hard solid with no appreciable water absorbency. Materials that are substantially non-water soluble, but still absorbent can be made. However, the use of gamma rays requires expensive equipment and time consuming procedures due to safety concerns, and the degree of cross-linking that is obtained is often difficult to control.

Several references have reported the use of chemical cross-linking groups as a method of avoiding the dangers and costs associated with the use of ionizing radiation. Chu (U.S. Pat. No. 3,963,605) reported a water-swellable, cross-linked poly(alkylene oxide) that was produced by h mixture of poly(ethylene oxide) with acrylic acid and a free radical initiator such as acetyl peroxide in a hydrocarbon solvent such as hexane, heptane, or cyclohexane. Another alternative was reported in Canadian Pat. No. 756,190, and involved cross-linking through a di-vinyl monomer in the presence of a free radical catalyst. The use of other crosslinking agents, such as a diacrylate, or methyl-bisacrylamide with a free radical inhibitor, has also been reported.

Lubricious coatings of cross-linked, hydrophilic polyurethane have been reported by Watson in U.S. Pat. No. 6,020,071. Another polyurethane coating is described by Tedeshchl et al., in EP 0992 252 A2, where a lubricious, drug-accommodating coating is described that is the product of a polyisocyanate; an amine donor, and/or hydroxyl donor; and an isocyanatosilane adduct having terminal isocyanate groups and an alkoxy silane. A water soluble polymer, such as poly(ethylene oxide), can optionally be present. Cross-linking causes a polyurethane or a polyurea network to form, depending upon whether the isocyanate reacts with the hydroxyl donors or the amine donors.

Despite these advances, there is still a need for a method to form a durable and plastic-like coating on an article where the coating is adherent to the article and yet has a high degree of water absorbency when contacted with an aqueous fluid. There is a particular need for such coatings that are biologically inert and nontoxic, are lubricious when moist, and can be formed under conditions that do not require irradiation or extreme temperatures. It is to such needs that the present invention is directed.

SUMMARY OF THE INVENTION

Briefly, therefore the present invention is directed to a novel method of forming a coating on an article, the method comprising contacting the article with a copolymer comprising a water soluble base polymer having graft polymerized thereto an organic moiety that includes a group that reacts with water to form a silanol group; and curing the copolymer to form a coating comprising the crosslinked copolymer on the article.

The present invention is also directed to a novel coating on an article, the coating comprising a crosslinked hydrogel that includes a copolymer comprising water soluble base polymers having graft polymerized thereto organic moieties that react with water to form a silanol group, the copolymer being crosslinked through the silanol groups of the organic moieties to form a coating that is absorbent, lubricious and substantially non-water soluble.

The present invention is also directed to a novel coated article comprising an article coated with a crosslinked hydrogel that includes a copolymer comprising water soluble base polymers having graft polymerized thereto organic moieties that react with water to form a silanol group, the copolymer being crosslinked through the silanol groups of the organic moieties to form a coating that is absorbent, lubricious and substantially non-water soluble.

The present invention is also directed to a novel coating solution comprising a mixture of a solvent and a copolymer comprising a water soluble base polymer having graft polymerized thereto an organic moiety that includes a group that reacts with water to form a silanol group.

Among the several advantages found to be achieved by the present invention, therefore, may be noted the provision of a method to form a durable and plastic-like coating on an article where the coating is adherent to the article and yet has a high degree of water absorbency when contacted with an aqueous fluid, and the provision of such a coating that is biologically inert and nontoxic, and is lubricious when moist, and can be formed under conditions that do not require irradiation or extreme temperatures.

DETAILED DESCRIPTION OF THE PREFERRED EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope and spirit of the invention. For instance, features illustrated or described as part of one embodiment, can be used on another embodiment to yield a still further embodiment.

Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

In accordance with the present invention, it has been discovered that an absorbent, lubricious, substantially non-water soluble coating can be placed on various articles by contacting the article with a solution of a copolymer comprising a water soluble base polymer having graft polymerized thereto an organic moiety that includes a group that reacts with water to form a silanol group, and then curing the copolymer to form a coating on the article that comprises the crosslinked copolymer. Coating solutions that include the copolymer and articles that have been coated with the novel coating are also included in the scope of the invention, as is the actual coating itself.

An important property of the coating is that it can be applied to almost any article without the use of dangerous ionizing radiation, or the exposure of the article to conditions of biologically irritating high or low pH values. In fact, the curing can be done by simply exposing the copolymer to moisture and then, in one embodiment, removing the moisture to form the crosslinked coating.

Application of the coating to articles such as fibers and fabrics—in particular to woven or nonwoven fabrics that are useful for bandages, medical drapes, diapers, feminine hygiene products and incontinence aids—is easily done and provides materials having the dual advantage of high structural strength plus the property of being highly absorbent and lubricious.

If it is desirable, various materials such as therapeutic agents, can be included in the coating as releasable components. With this feature, the coating is adapted to act as a controlled release matrix for the releasable component, and to release the component for contact with, for example, a wound bed upon which a dressing containing the novel coating has been placed.

A copolymer that is useful for the present coating comprises a graft copolymer of a water soluble base polymer to which is engrafted an amount of an organic moiety that includes a group that reacts with water to form a silanol group. Suggested water-soluble base polymers useful in the present invention include, but are not limited to, poly (alkylene oxides), such as poly(ethylene oxide) ("PEO"), poly(ethylene glycols), block copolymers of ethylene oxide and propylene oxide, poly(vinyl alcohol) and poly(alkyl vinyl ethers). These water-soluble base polymers are capable of graft polymerization with an organic moiety containing a trialkoxy silane functional group or another such moiety that reacts with water to form a silanol group. One particularly useful water-soluble base polymer for use in the present invention is PEO. A process for the graft polymerization of PEO with methacryloxypropyl trialkoxy silane followed by cross-linking upon exposure to moisture is shown below.

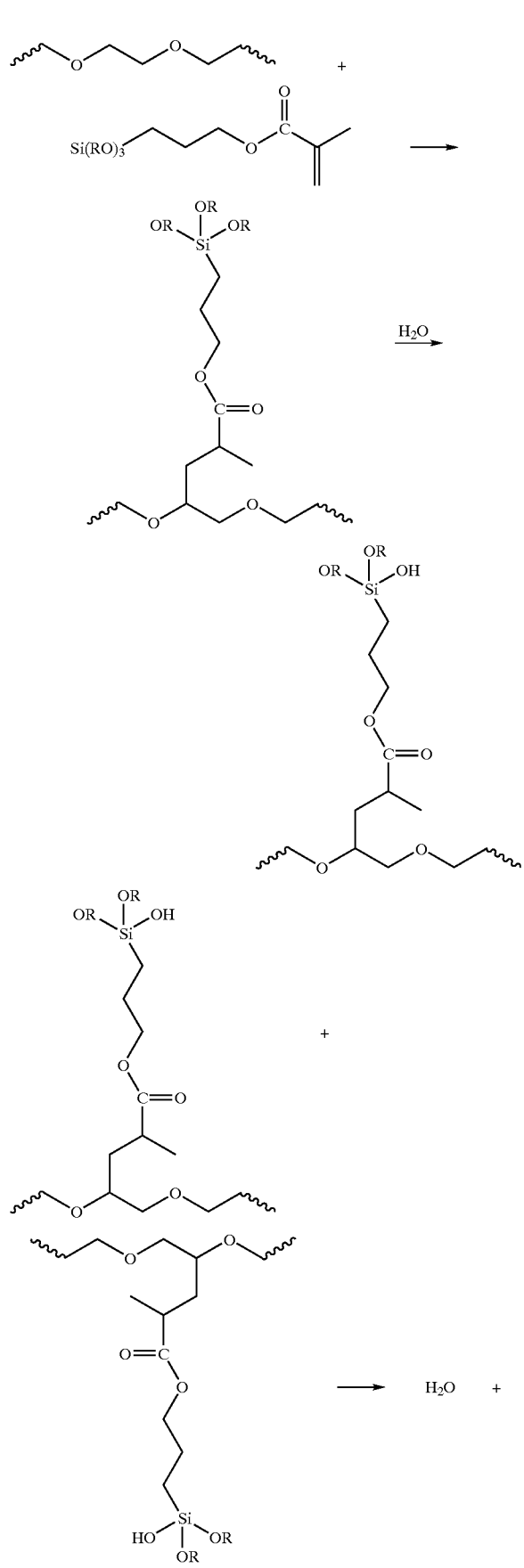

Since crosslinking of a silane graft-modified PEO does not normally occur during thermal processing, the graft-modified PEO that is useful for the coatings of the present invention provides for more robust thermal processing into functional forms. Furthermore, since the process of forming a silane graft-modified PEO does not require the use of aqueous solutions, there are no costly and time consuming evaporation steps involved.

Desirable water soluble base polymers and resins useful for graft modification for use in coatings in accordance with the present invention include, but are not limited to, PEO resins having initial reported approximate molecular weights ranging from about 10,000 g/mol to about 8,000,000 g/mol as determined by rheological measurements. Such PEO resins are commercially available from, for example, Union Carbide Corporation having offices in Danbury, Conn., and are sold under the trade designations POLYOX® 205, POLYOX® N-10, POLYOX® N-80, POLYOX® WSR N-750, POLYOX® WSR N-12K and POLYOX® UCARFLOC® Polymer 309.

The coatings of the present invention can be made from commercially available PEO resins when modified as described herein. The PEO resins useful for the subject coatings include, but are not limited to, PEO resins having initial reported approximate molecular weights ranging from about 50,000 g/mol to about 600,000 g/mol. Higher molecular weights are desired for increased mechanical and physical properties and lower molecular weights are desired for ease of processing. Desirable PEO resins for use in coatings have molecular weights ranging from 50,000 to 600,000 g/mol before modification and more desired PEO resins have molecular weights ranging from 50,000 to 300,000 g/mol before modification. The PEO compositions modified from PEO resins within the above resins provide desirable balances between mechanical and physical properties and processing properties. Four PEO resins within the above preferred ranges are commercially available from Union Carbide Corporation and are sold under the trade designations POLYOX® N-205 ,POLYOX® N-750, POLYOX®

WSR N-10 and POLYOX® WSR N-80. These four resins have reported approximate molecular weights, as determined by Theological measurements, of about 100,000 g/mol to 600,000 g/mol.

Other PEO resins available from, for example, Union Carbide Corporation, within the above approximate molecular weight ranges are sold under the trade designations WSR N-750, WSR N-3000, WSR-3333, WSR-N-12K, WSR-N-60K, WSR-301, WSR Coagulant POLYOX®: Water Soluble Resins, Union Carbide Chemicals & Plastic Company, Inc. (1991). Both PEO powder and pellets of PEO can be used in this invention since the physical form of PEO does not affect its behavior in the melt state for grafting reactions. This invention has been demonstrated by the use of PEO in powder form as supplied by Union Carbide. However, the PEO resins to be modified may be obtained from other suppliers and in other forms, such as pellets. The PEO resins and modified compositions may optionally contain various additives, such as, plasticizers, processing aids, rheology modifiers, antioxidants, UV light stabilizers, pigments, colorants, slip additives, antiblock agents, etc., which may be added before or after modification.

Organic monomers capable of graft polymerization with the water soluble base polymers described above and which also contain a functional group or moiety that reacts with water to form a silanol group are useful for the synthesis of copolymers that can be used to form the coatings of the present invention. One such functional group that can react with water to form a silanol group is a trialkoxy silane functional group. The trialkoxy silane functional group can have the following structure:

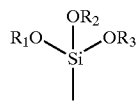

wherein $R_1$, $R_2$ and $R_3$ are the same or different alkyl group, each independently having 1 to 6 carbon atoms.

The term "monomer(s)" as used herein includes monomers, oligomers, polymers, mixtures of monomers, oligomers and/or polymers, and any other reactive chemical species which is capable of covalent bonding with the parent polymer, PEO. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane. Methacryloxypropyl trimethoxy silane is commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects to PEO and are effective monomers for grafting in accordance with the copolymers that are useful in the coatings and methods of the present invention.

The amount of organic monomer having trialkoxy silane functional groups or silanol-forming functional groups relative to the amount of PEO may range from about 0.1 to about 20 weight percent of monomer to the weight of PEO. Desirably, the amount of monomer should exceed 0.1 weight percent in order sufficiently to improve the processability of the PEO. A range of grafting levels is demonstrated in the Examples. Typically, the monomer addition levels are between about 0.25% and about 15% of the weight of the base PEO resin; particularly, between about 0.5% and about 10% of the weight of the base PEO resin; and especially, between about 1.5% and about 6.0% of the weight of the base PEO resin.

A variety of initiators may be useful in forming the graft copolymer from the water soluble base polymer and the monomer. When grafting is achieved by the application of heat, as in a reactive-extrusion process, it is desirable that the initiator generates free radicals through the application of heat. Such initiators are generally referred to as thermal initiators. For the initiator to function as a useful source of radicals for grafting, the initiator should be commercially and readily available, stable at ambient or refrigerated conditions, and generate radicals at reactive-extrusion temperatures.

Compounds containing an O—O, S—S, or N=N bond may be used as thermal initiators. Compounds containing O—O bonds; i.e., peroxides, are commonly used as initiators for graft polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis (cyclohexanecarbonitrile) may be used as the initiator. Graft copolymers that are useful in the subject coatings have been demonstrated in the following Examples by the use of a liquid, organic peroxide initiator available from R. T. Vanderbilt Company, Inc. of Norwalk, Conn., sold under the trade designation VAROX DBPH peroxide which is a free radical initiator and comprises 2,5-bis(tert butylperoxy)-2,5-dimethyl hexane along with smaller amounts of di(tert butylperoxide). Other initiators may also be used, such as LUPERSOL® 101 and LUPERSOL® 130 available from Elf Atochem North America, Inc. of Philadelphia, Pa.

A variety of reaction vessels may be useful to produce the copolymers useful for the subject coatings. The modification of the PEO can be performed in any vessel as long as the necessary mixing of PEO, the monomer and the initiator is achieved and enough thermal energy is provided to affect grafting. Desirably, such vessels include any suitable mixing device, such as Brabender Plasticorders, Haake extruders, Bandbury mixers, single or multiple screw extruders, or any other mechanical mixing devices which can be used to mix, compound, process or fabricate polymers. One useful reaction device is a counter-rotating twin-screw extruder, such as a Haake extruder available from Haake, 53 West Century Road, Paramus, N.J. 07652. Another is a co-rotating, twin-screw extruder, such as a ZSK-30 twin-screw, compounding extruder manufactured by Werner & Pfleiderer Corporation of Ramsey, N.J. It should be noted that a variety of extruders may be used to modify the PEO provided that sufficient mixing and heating occur.

The inventors have discovered that the copolymers described above can be used to form a coating on an article, the method involves contacting the article with a copolymer of a water soluble base polymer having graft polymerized thereto an organic moiety that includes a group that reacts with water to form a silanol group; and curing the copolymer to form a coating comprising the crosslinked copolymer on the article.

In one embodiment, the method for contacting an article to be coated with the copolymers described above is to form a solution of the copolymer in a solvent and place a film of solution on the article. As that term is used herein, "solution" should be understood to include true solutions, emulsions and dispersions.

It is believed that this coating solution is also within the scope of the present invention. The coating solution comprises a mixture of a solvent and a copolymer comprising a water soluble base polymer having graft polymerized thereto an organic moiety that includes a group that reacts with water to form a silanol group. The water soluble base polymers and organic moieties that are useful for the present coating solutions include those that have been discussed above. In particular, solutions containing poly(ethylene oxide) engrafted with 3-methacryloxypropyl tris (methoxyethoxy) silane have been found to be desirable.

When the copolymer is placed into solution in a solvent, it is believed that almost any liquid can be used. It is desirable that the liquid be an organic solvent, such as an alcohol, ketone, aldehyde, alkane, alkene, aromatic, or mixture thereof, or be water. Water can also be used in combination with an organic solvent. When a mixture of water and an organic solvent is used as the solvent, the water should be present in an amount of from about 5% to about 100% by weight. It is desirable that pure water be used as the solvent.

Variable amounts of the copolymer can be used to form the solution. It is believed that solutions containing from about 0.1% to about 10% by weight of the copolymer can be used, and solutions containing about 1% to about 8% by weight are desirable.

After the copolymer has been placed into solution in a solvent, the solution is then contacted with the article to be coated so as to place a film of the solution on the article. This can be done by dipping, spraying, printing, painting, or immersing the article with or in the solution. A common way to apply the film to the article is to simply dip the article into the solution and allow any excess solution to drain from the article. This step can be carried out once, or it may be repeated any number of times. If desirable, the copolymer in the film may be cured after a film has been applied, and then the application of another film of the copolymer may be repeated in order to build up a coating of the desired thickness.

After a film of the solution containing the copolymer has been applied to the article, the copolymer is cured to form a cross-linked hydrogel coating. The copolymer can be cured by removing solvent from the copolymer. One method of removing liquid that results in curing the copolymer is to evaporate the solvent. A common method for carrying out the evaporation is by drying the article. Such drying is commonly done in air under ambient conditions, but the article can be placed in an oven or other temperature and/or humidity controlled space in order to control the drying. As the solvent is removed from the film, silanol groups of adjacent copolymers form bonds to cross-link the structure into a hydrogel.

As an alternative, removal of the solvent can be carried out by any method, such as, for example, absorption, chelation, sequestration or chemical reaction.

In an alternative method, the coating can be applied to the article by applying a film of liquid to the article, where the film contains the copolymer in un-crosslinked form. This can be done by melting the copolymer and applying the molten copolymer to the article to form the film. Alternatively, the copolymer may be dispersed in a non-aqueous solvent to form a dispersion or emulsion, and the dispersion or emulsion can be applied to the article to form the film.

When the un-crosslinked copolymer is used to form a film on an article it is normally desirable that this be carried out under substantially water-free conditions in order to avoid premature cross-linking of the copolymer. In fact, it is often desirable that the film be applied under conditions that are substantially anhydrous.

It is normal for the film that is applied to the article to be coated to be applied in such a manner that it substantially covers the exterior surface of the article. Of course, when a coating is to be placed on the interior surface of an article, it is necessary that the film also contact that surface. In fact, any surface that is to be coated should be covered by the film.

After the film containing the un-crosslinked copolymer has been applied, it can be cured by contacting the film with water. This can be done in any manner, such as dipping, spraying, misting, or exposing the article to high humidity conditions. When it is said that the article is to be contacted with water, any form of water is included—such as liquid water or water vapor.

One important characteristic of the curing step of the novel coating method is that it is free of the need for the use of ionizing radiation, such as gamma radiation. It can also be done at ambient temperature and pressure. Moreover, it can be carried out at normal, physiological pH values, for example, at a neutral pH, or at a pH between about 6 and about 8. Benefits of this feature include that the curing can be done while the film is in contact with a wound, and that there are no residual fluids having biologically irritating low or high pH values that could leach out of a dressing and irritate a wound.

The copolymer is cured by the method described above to form a coating on an article, the coating comprising a crosslinked hydrogel that includes a copolymer comprising water soluble base polymers having graft polymerized thereto organic moieties that react with water to form a silanol group, the copolymer being crosslinked through the silanol groups of the organic moieties to form a coating that is absorbent, lubricious and substantially non-water soluble.

When it is said that the coating is "absorbent", what is meant is that the coating can absorb water. As will be shown in the Examples, which follow, the present coatings are capable of absorbing their own weight in water, or even many times their own weight. It is believed that this is an advantage of the present coatings, particularly when they are used in applications where moisture absorption and control are important—such as in bandages, diapers, and the like.

When it is said that the coating is "lubricious", it is meant that the outer surface of the coating has a smooth and slippery quality when wet.

When it is said that the coating is "substantially non-water soluble", it is meant that the cured coating has a solubility in water at 25° C. of less than 40% by weight, desirably, less than 4% by weight.

It is believed to be desirable that the copolymer that is used to form the novel coating contains the organic moiety that is engrafted onto the water soluble base polymer in an amount that is within a range of about 0.5 to about 10 percent by weight of the water soluble base polymer. It has been found that resins with higher grafting levels produce a stiffer gel with high lubricity and less absorbent capacity while lower grafting levels produce softer, more absorbent gels on the surface of the substrate.

In some instances, it is desirable that the coating be translucent, or even be transparent. It can then be used on lenses or windows, and can have an antifogging property so that the coated lens or window is resistant to fogging.

When the coating is used on tubing and articles that come into contact with blood and other bodily fluids, it is desirable that the coating be non-thrombogenic or anti-thrombogenic.

Another feature of the present coating is that it can act as a reservoir for releasable components that are to be delivered from the coating to a region outside of the coating, such as, for example, a wound. In this embodiment, the coating can act to provide a controlled release of such compounds as therapeutic agents, bioactive agents, antibiotics, bactericides, fungicides, drugs, growth factors, peptides, proteins, enzymes, emollients, antiseptics, anti-oxidants, wetting agents, and mixtures thereof.

Articles that have a coating as described above invention are also to be included in the present invention. Such coated articles comprise an article coated with a crosslinked hydrogel that includes a copolymer comprising water soluble base polymers having graft polymerized thereto organic moieties that react with water to form a silanol group, the copolymer being crosslinked through the silanol groups of the organic moieties to form a coating that is absorbent, lubricious and substantially non-water soluble.

It is believed that the novel coating can be placed on almost any type of article, and useful articles include articles that are metal, glass, natural or synthetic polymer, natural fiber, wood, another coating or paint, or a mixture thereof. As noted above, the article can be a transparent lens or window. In addition, the lubricity of the subject coating can be advantageous when the coated article is the water-contacting surface of a pipe, tube, pipeline, boat hull, submarine, torpedo, fishing line, fishing lure, water ski, propeller, or any other article that carries or contacts moving water. By using the novel coating, fluid friction caused by the article moving in relation to the water can be reduced and the cost or effort of such movement can also be reduced.

The novel coating can also be applied to such articles as medical instruments, bandages, drapes, fabrics, fibers, foams, films, tubing, catheters, shunts, artificial organs, dialysis apparatus, surgical instruments, stents, indwelling splints, and guide wires.

When the coated article is a fiber, it has been found to be useful for the underlying fiber to be coated to be one that is produced from poly(propylene), poly(ethylene terephthalate), poly(lactic acid), or rayon.

However, the present invention is not limited to these or any particular polymer or material from which to form the fibers. For example, various other materials, including the following, may be used: polyethylene, polyesters, polybutane, polymethyldentene, ethylenepropylene co-polymers, polyamides, tetrablock polymers, styrenic block copolymers, polyhexamethylene adipamide, poly-(oc-caproamide), polyhexamethylenesebacamide, polyvinyls, polystyrene, polyurethanes, thermoplastic polymers, polytrifluorochloroethylene, ethylene vinyl acetate polymers, polyetheresters, polyurethane, polyurethane elastomerics, polyamide elastomerics, polyamides, viscoelastic hot melt pressure sensitive adhesives, cotton, and hemp. In addition, such materials may be utilized to extrude single-constituent, bi-constituent, and bi-component fibers, in a variety of cross-sectional shapes, which may be coated with the novel coating of the presently described invention.

Other exemplary elastomeric materials that may be used include polyurethane elastomeric materials such as those available under the trademark ESTANE from B.F. Goodrich & Co., polyamide elastomeric materials such as those available under the trademark PEBAX from the Rilsan Company, and polyester elastomeric materials such as those available under trade designation HYTREL from E.I. DuPont De Nemours & Company.

However, the fibers that are useful in the present invention are not limited to only such elastomeric materials. For example, various latent elastic materials such as the Arnitel-brand polymers may be utilized to provide the necessary elasticity characteristics to the continuous filaments.

The materials utilized to form the continuous fibers may also be utilized in forming woven or non-woven fabrics that can be substrates for the novel coating. In particular, various webs may be utilized that are formed from elastomeric or nonelastomeric fibers. Various polyester elastic materials are, for example, disclosed in U.S. Pat. No 4,741,949 to Morman et al. Other useful elastomeric polymers also include, for example, elastic copolymers of ethylene and at least one vinyl monomer such as, for example, vinyl acetates, unsaturated aliphatic monocarboxylic acids, and esters of such monocarboxylic acids. The elastic copolymers and formation of elastomeric fibers from these elastic copolymers are disclosed in, for example, U.S. Pat. No. 4,803,117.

The nonwoven fabrics that are useful in the present invention may be a mixture of elastic and nonelastic fibers or particulates. For example, U.S. Pat. No. 4,209,563 describes the process by which elastomeric and nonelastomeric fibers are commingled to form a single coherent web of randomly dispersed fibers. Another example of such an elastic composite web is shown in U.S. Pat. No. 4,741,949, wherein an elastic nonwoven material is described as including a mixture of meltblown thermoplastic fibers and other materials. The fibers and other materials may be combined in the forming gas stream in which the fibers are borne so that an intimate entangled commingling of fibers and other materials, e.g., wood pulp, staple fibers or particulates such as, for example, activated charcoal, clays, starches, or hydrocolloid (hydrogel) particulates, occurs prior to collection of the fibers upon a collecting device to form a coherent web of randomly dispersed fibers Various processing aids may also be added to the elastomeric polymers utilized in the present invention. For example, a polyolefin may be blended with the elastomeric polymer (e.g., the A-B-A elastomeric block copolymer) to improve the processability of the composition. The polyolefin should be one which, when so blended and subjected to an appropriate combination of elevated pressure and elevated temperature conditions, is extrudable in blended form with the elastomeric polymer. Useful blending polyolefin materials include, for example, polyethylene, polypropylene and polybutene, including ethylene copolymers, propylene copolymers and butene copolymers. A particularly useful polyethylene may be obtained from the U.S.I. Chemical Company under the trade designation Petrothene NA 601 (also referred to herein as PE NA 601 or polyethylene NA 601). Two or more of the polyolefins may be utilized. Extrudable blends of elastomeric polymers and polyolefins are disclosed in, for example, U.S. Pat. No. 4,663,220.

The elastomeric materials that are utilized to form the elastomeric filaments may have sufficient tackiness to enhance the bonding strength of the laminate by allowing a degree of autogenous bonding. For example, the elastomeric polymer itself may be tacky when formed into fibers and/or filaments or, alternatively, a compatible tackifing resin may be added to the extrudable elastomeric compositions described above to provide tackified elastomeric fibers and/or filaments that autogenously bond. Various known tackifying resins and tackified extrudable elastomeric compositions may be employed, such as those described in U.S. Pat. No. 4,787,699.

Any tackifier resin can be used that is compatible with the elastomeric polymer and can withstand the extrusion processing conditions. If the elastomeric polymer (e.g., A-B-A elastomeric block copolymer) is blended with processing aids such as, for example, polyolefins or extending oils, the tackifier resin should also be compatible with those processing aids. Generally, hydrogenated hydrocarbon resins exhibit enhanced temperature stability and, thus, may be desirable tackifiers. REGALREZ™ hydrocarbon and ARKON™ series tackifiers are examples of hydrogenated hydrocarbon resins. ZONATAK™ 501 lite is an example of a terpene hydrocarbon. REGALREZ™ hydrocarbon resins are available from Hercules Incorporated. ARKON™ series resins are available from Arakawa Chemical (U.S.A.) Incorporated. Of course, the present invention is not limited to use of such tackifying resins, and other tackifying resins that are compatible with the other components of the composition and that can withstand the processing conditions may also be used.

A structure that utilizes such an elastomer as a substrate on which to deposit a novel coating has the advantage of having an inexpensive core material to provide the structural characteristics and the novel coating to provide absorbency and lubricity. Such fibers can be formed into either woven or nonwoven fabrics.

Woven and nonwoven fabrics having a coating or filling of the present coating offer a number of advantages. For example woven gauze having a subject hydrogel coating provides high absorbency coupled with high integrity and non-adherence to the wound.

Surge material can be coated on one side to provide a structure having gradient hydrophilicity and absorbency. In addition, if desired, a hydrophilic/absorbent adhesive can be used to secure the surge to the retention layer to eliminate gaps and assure intimate contact.

In an alternative embodiment, surge material could simply be saturated with the coating solution to provide a pseudo-foam wound dressing having the benefit of being a low cost alternative to foam, but with high absorbency.

It is believed that useful articles that can act as substrates for the novel coating include bandages, drapes, diapers, feminine hygiene products, or incontinence aids.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples.

General Procedures

In the examples all percentages are given on a weight basis unless otherwise indicated.

All molecular weights are given on a weight average basis unless otherwise indicated.

Water absorbency under unrestrained conditions (free swell) of copolymers that can be used in the subject coatings was tested according to the following method. A sample of film or resin pellet with a weight of 30 to 50 milligrams is weighed in the dry state to the nearest tenth of a milligram. The test sample is place in a 500 ml bottle to which 100 ml of distilled water is added. The bottle is shaken on a laboratory shaker for 30 minutes at room temperature. The contents of the bottle are filtered under vacuum with a Beuchner funnel using Whatman 55 mm filter paper. The swollen sample is removed from the filter paper and weighed to the nearest milligram. Gram per gram uptake is calculated as the wet weight of recovered (insoluble) material, divided by the initial dry weight of the sample, minus 1. Generally, the average of 5 replicates is reported. A similar procedure is used with 0.9% saline replacing distilled water.

Uptake of simulated menses or saline solution was determined for the coatings as follows: Samples of the copolymer to be tested were weighed and then soaked in 20 ml of saline or menses simulant composed of swine blood of controlled hemocrit with albumin added to simulate the visco-elastic properties of menses. The samples were soaked for 30 minutes, removed, the excess fluid was drained from the surface, and the wet samples were then weighed. This weight is used to calculate the saturated uptake. The sample is then placed under a pressure of 0.5 psi and then weighed again to determine the blotted uptake after expressed fluid has drained from the sample. The amount of fluid that remains in the sample is used to calculate the fluid uptake at 0.5 psi.

EXAMPLE 1

This example illustrates the synthesis of a graft copolymer from poly(ethylene oxide) engrafted with 3-(trimethoxysilyl) propyl methacrylate that is useful in the coatings of the present invention.

Polyethylene oxide ("PEO"), supplied by Union Carbide under the name POLYOX Water Soluble Resins, was used. POLYOX WSR-205 having a molecular weight of about 600,000 g/mol was used in powder form. The reactive polar vinyl monomer used was 3-(trimethoxysilyl) propyl methacrylate supplied by Aldrich Chemical Company and manufactured by Dow Coming under the trade name, Dow Corning Z-6030 Silane. The peroxide initiator used was Varox DBPH, supplied by R.T. Vanderbilt Company, Inc.

The monomer is composed of two functional groups. The methacrylate function reacts with PEO after a free radical site is initiated with peroxide. The resultant modified PEO resin is still thermally processable as long as it is kept relatively dry. The crosslinking takes place from the other end of the molecule at the alkoxysilane function. The alkoxysilane is readily hydrolyzed into a more reactive silanol and the silanol condenses with another silanol to form a cross-linked network. Because the grafting monomer has three alkoxysilanes, each graft site is theoretically capable of forming three crosslinks. Use of this type of grafting monomer provides a modified resin, which, while kept relatively dry, can be fabricated into useful structures, and then, when exposed to humid air, become crosslinked.

The result is a material that retains the versatility of thermal processability into a variety of structures along with the capability of using those structures for absorbency. This unusual combination of features is available because the crosslinked, hydrophilic network is generated after the structure is fabricated.

A bench-scale HAAKE twin-screw extruder was used. This unit contains a set of custom-made, counter-rotating conical twin screws. Screw Design for the HAAKE Extruder:

A general characteristic description is provided in Table 1 since the exact dimensions may be proprietary to the extruder manufacturer.

TABLE 1

Extruder characteristics.

| Sections | Descriptions |
|---|---|
| Section 1: | A double flighted forward pumping section: Large screw lead (pitch) and a high helix angle |
| Section 2: | A double flighted forward pumping section: Screw pitch is smaller than Section 1 |
| Section 3: | A double flighted forward pumping section: Screw pitch is smaller than Section 2 |
| Section 4: | A double flighted and notched reversed pumping section One complete flight with notches |
| Section 5: | A double flighted notched forward pumping section Two complete flights |
| Section 6: | A double flighted forward pumping section Screw pitch is between sections 1 and 2. |

The die has two openings of 3 mm in diameter, which are separated by 10 mm. The strands were cooled in air and subsequently pelletized. The feed section was not heated, rather it was cooled by water. The extruder has three heating sections from the feeding section towards the die designated as Zone 1, Zone 2, and Zone 3. The die was designated as Zone 4

The first reactive extrusion was done on a HAAKE twin screw extruder of 10/1 L/D with custom designed screws (described above) at a rate of 5 pounds per hour. The pelletized POLYOX 205 was metered into the throat of the extruder at a rate of 37.8 g/min with a K-Tron feeder. In the same manner, Varox DBPH peroxide was metered at a rate equivalent to 0.25 weight percent of the POLYOX 205 and the Z-6030 silane was metered in with an Eldex pump at a rate of 2 to 5 weight percent of the POLYOX 205. The temperature profile for the heating zones were 150°, 160°, 160°, and 170° C. The screw speed was 150 rpm. The strands were cooled in air using a fan-cooled conveyer belt. The solidified strands of the grafted POLYOX 205 were then pelletized using a Conair pelletizer.

The sample pellets from this experiment were stored under ambient conditions for four months and then under high humidity (33° C. and 80% relative humidity) for seven days. The resin samples were tested to determine the ultimate gel fraction according to the procedure described below. The gel fraction is the portion of the sample that is cross-linked and no longer soluble in water. The soluble fraction is equal to 1-(gel fraction).

Gel Fraction Test

A sample of film or resin pellet with a weight of 30 to 50 milligrams is weighed in the dry state to the nearest tenth of a milligram. The test sample is place in a 500 ml bottle to which 100 ml of distilled water is added. The bottle is shaken on a laboratory shaker for 30 minutes at room temperature. The contents of the bottle are filtered under vacuum with a Beuchner funnel using Whatman 55 mm filter paper (catalogue # 1001 55) which was pre-dried at 60° C. and weighed to the nearest tenth of a milligram. The insoluble portion of the sample is dried along with the filter paper at 60° C. for two hours and then weighed to determine the dry weight of insoluble material.

Gel fraction or percent gel is taken as the dry weight of recovered (insoluble) material divided by the initial dry weight of the sample. Generally, the average of 5 replicates is reported in Table 2 below:

TABLE 2

Gel fraction in several samples of graft copolymer

| Sample | Weight percent Z6030 | Weight percent Varox DBPH | Extruder Pressure (psi) | Gel Fraction |
|---|---|---|---|---|
| 1-1 | 0 | 0 | 530 | 0 |
| 1-2 | 2 | 0.15 | 330 | 0.91 |
| 1-3 | 5 | 0.25 | 430 | Not tested |

The addition of the monomer and peroxide initiator results in a reduction in extruder pressure compared to the control. The reduced pressure is indicative of reduced melt viscosity. This result indicates that the PEO has been modified into a form that is water-absorbent and not completely water-soluble like the control resin (sample 1-1).

EXAMPLE 2

The following samples were prepared using the same method and extruder temperatures as described above in Example 1 and using the proportions of ingredients indicated in Table 3 below. Since the first sample resulted in low extruder pressure, the temperatures were reduced to bring the extruder pressure into the proper range.

TABLE 3

Production parameters for extrusion/reaction.

| Sample | Weight % vinyl triethoxy silane | Weight % Varox DBPH | Extruder pressure (psi) | Comments, Observations |
|---|---|---|---|---|
| 2-1-a | 5 | .25 | 92 | Very low pressure, temperatures reduced to 120, 130, 130, 140 |
| 2-1-b | 5 | .25 | 270 | Low melt viscosity |
| 2-2 | 2 | .15 | 350 | Slight pressure increase |
| 2-3 | 0 | 0 | 700 | P205 control, high pressure, rough strands |

Pellets from samples 2-1-b, 2-2 and 2-3 were stored for approximately ten weeks under laboratory conditions, exposed to ambient humidity. All three samples aged under these conditions, dissolved in water after standing overnight.

The resin samples prepared with triethoxy vinyl silane remained water-soluble. This result suggests that this monomer was not grafted onto P205 under the same conditions that were effective for grafting Z6030. The significant reduction in melt pressure and melt viscosity indicates that chain scission of the PEO was occurring rather than grafting. Different conditions or initiators may be needed to induce grafting between PEO and triethoxy vinyl silane.

EXAMPLE 3

A third reactive extrusion experiment was conducted to evaluate the effect of higher addition level of the Z6030 monomer along with proportionately higher addition of the peroxide initiator. The same screw design and production rate as Example 1 was used. The pelletized POLYOX 205 was metered into the throat of the extruder at a rate of 37.8 g/minute with a K-Tron feeder. Dow Corning Z-6030 Silane was metered into the throat of the extruder with an Eldex pump at a rate of 3.78 g/minute, equivalent to ten weight percent of the POLYOX 205. In the same manner, Varox DBPH peroxide was metered at a rate equivalent to 0.40 weight percent of the POLYOX 205. A second code was run at five weight percent addition of Z6030 with Varox DBPH peroxide metered at a rate equivalent to 0.33 weight percent of the POLYOX 205. The temperature profile for the heating zones were 150°, 160°, 160°, and 170° C. The strands were cooled in air using a fan-cooler conveyor belt. The solidified strands of the grafted POLYOX 205 were then pelletized on a Conair pelletizer.

The sample descriptions and gel fraction results are shown in the Table 4 below. These gel fraction results were obtained after six months at ambient conditions followed by one week at 80% relative humidity.

TABLE 4

Gel fractions generated in samples of a graft copolymer.

| Sample | Weight % Z6030 | Weight % Varox DBPH | Extruder pressure (psi) | Gel Fraction |
| --- | --- | --- | --- | --- |
| 3-1 | 10 | .40 | 420 | .92 |
| 3-2 | 5 | .33 | 450 | .95 |

These result indicate that five percent Z6030 is sufficient monomer to provide a nearly crosslinked, PEO gel.

EXAMPLE 4

The Z6030 reactive grafting was done with a ZSK-30 extruder. A ZSK-30 co-rotating, twin-screw extruder (manufactured by Werner & Pfleiderer) with 14 barrel sections and 1338 mm total processing section length was used. The first barrel was not heated, but cooled by water. The peroxide was injected into barrel # 5 and the Z6030 monomer was injected into barrel # 6. Both chemicals were injected via a pressurized nozzle injector. The die has four openings of 3 mm in diameter, which are separated by 7 mm. Polymer strands were extruded onto an air-cooling belt and subsequently pelletized.

The following extruder barrel temperatures (in ° C.) were set to the following levels during the extrusion as shown in Table 5:

TABLE 5

Extruder conditions during reactive grafting.

| Zone 1 | Zone 2 | Zone 3 | Zone 4 | Zone 5 |
| --- | --- | --- | --- | --- |
| 166° | 180° | 180° | 180° | 180° |

The polymer melt temperature was 195°–205° C. The polymer cooled on a stainless steel cooling belt and subsequently pelletized.

TABLE 6

ZSK-30 Screw Configuration for Reactive Extrusion

| Element No. | Description | Element No. | Description |
| --- | --- | --- | --- |
| 1 | PKR 10 | 31 | KB45/5/14 |
| 2 | 20/10 | 32 | KB 45/5/14 |
| 3 | 42/42 | 33 | 20/20 |
| 4 | 42/42 | 34 | 20/20 |
| 5 | 28/28 | 35 | 20/20 |
| 6 | 28/28 | 36 | 28/28 |
| 7 | 20/20 | 37 | 28/28 |
| 8 | 20/20 | 38 | 28/28 |
| 9 | KB 45/5/28 | 39 | 20/20 |
| 10 | KB 45/5/14 | 40 | 20/10 LH |
| 11 | 28/28 | 41 | 42/42 SK |
| 12 | 28/28 | 42 | 42/42 SK |
| 13 | 28/28 | 43 | 42/42 |
| 14 | 28/28 | 44 | 20/20 |
| 15 | 20/20 | 45 | 20/20 |
| 16 | 28/28 | 46 | 20/20 |
| 17 | 28/28 | 47 | 20/20 |
| 18 | 20/20 | 48 | 20/20 |
| 19 | KB 45/5/42 | 49 | 20/20 |
| 20 | 28/28 | 50 | 20/20 |
| 21 | 20/20 | 51 | 20/20 |
| 22 | KB 45/5/28 | 52 | 20/20 |
| 23 | KB 45/5/14 LH | 53 | 20/10 |
| 24 | 28/28 | 54 | 20/10 |
| 25 | 20/20 | 55 | 20/10 |
| 26 | 20/20 | 56 | 20/10 |
| 27 | 28/28 | 57 | 20/10 |
| 28 | 28/28 | 58 | 20/10 |
| 29 | 20/20 | 59 | 20/10 |
| 30 | 20/20 | 60 | 14/14 | the PEO powder resin was fed into the ZSK-30 extruder with a K-Tron volumetric feeder at a throughput of 20 lbs/hr. The modified PEO strands were cooled between stainless steel belts that were cooled with water from the opposite side followed by pelletization. The results are shown in Table 7 below:

TABLE 7

Gel characteristics as a function of grafting variables.

| Sample | Weight % Z6030 | Weight % Varox DBPH | Extruder pressure (psi)/% torque/melt temperature ° C. | Gel Fraction |
| --- | --- | --- | --- | --- |
| 4-1 | 5.6 | .165 | 320/46%/214 | 0.94 |
| 4-2 | 5.6 | .33 | 320/46%/216 | Not tested |
| 4-3 | 11.3 | .33 | 380/47%/218 | Not tested |
| 4-4 | 11.3 | .66 | 390/48%/216 | 0.96 |

The variation in monomer and peroxide levels had minimal effect on the process data for pressure and torque. Gel fraction for samples 4-1 and 4-4 was tested after four months at ambient temperature and humidity and one week at elevated humidity and temperature (33° C. and 89% relative humidity).

EXAMPLE 5

Another reactive extrusion run on the ZSK-30 was designed to determine the effect of peroxide initiator addition and screw rpm, which determines residence time for the reaction, upon the resin properties. The silane monomer addition level was held constant at 1.3 mole percent (based on moles of ethylene oxide repeat) or 7.3 weight percent. The standard settings for temperature were the same as described in Example 4.

The settings for the experimental variables and the process data collected during the experiment are shown in Table 8, below.

TABLE 8

Variable Settings and Process Data

| Run# | VARIABLE Rpm | SETTINGS Wt. % Peroxide | PROCESS Melt Temp(° C.) | RESPONSE Percent of maximum Torque | DATA Melt Pressure |
|---|---|---|---|---|---|
| 5-1 | 300 | 0.22 | 210 | 45 | 600 |
| 5-2 | 100 | 0.22 | 200 | 85 | 810 |
| 5-3 | 100 | 0.13 | 200 | 86 | 830 |
| 5-4 | 300 | 0.13 | 205 | 42 | 700 |
| 5-5 | 200 | 0.17 | 205 | 50 | 800 |
| 5-6 | 100 | 0.13 | 201 | 86 | 890 |
| 5-7 | 300 | 0.13 | 206 | 43 | 700 |
| 5-8 | 300 | 0.22 | 206 | 42 | 600 |
| 5-9 | 100 | 0.22 | 199 | 85 | 780 |

The process data in Table 8 indicates a significant effect of the screw rpm upon the torque. Note that a reduction in rpm from 300 to 100 results in the torque readings increasing to nearly double. A significant, but less dramatic increase is observed in the melt pressure at the reduced rpm setting. Changes in the peroxide addition level had minimal effect on torque or pressure within the range studied.

Gel fraction results 165 hours cure at 33° C. and 80% relative humidity are shown in Table 9 below:

TABLE 9

Gel fraction results for several resins.

| Resin Sample | rpm | Weight % Varox DBPH | Gel Fraction |
|---|---|---|---|
| 5-6 | 100 | 0.13 | 0.87 |
| 5-7 | 300 | 0.13 | 0.82 |
| 5-8 | 300 | 0.22 | 0.84 |
| 5-9 | 100 | 0.22 | 0.85 |

EXAMPLE 6

To provide a modified PEO resin suitable for fiber spinning, a lower molecular weight PEO, POLYOX N-80, was used as the starting resin for reactive grafting on the ZSK-30 extruder. The initial molecular weight of this resin was 200,000 g/mol. Temperature settings for the extruder were the same as Examples 4 and 5. Other process settings are shown in the Table 10 below.

TABLE 10

Process settings for extruder reactive/grafting.

| Resin Sample | Wt % Z6030 | Wt % Varox DBPH | rpm | Process Data Pressure/torque | Gel Fraction |
|---|---|---|---|---|---|
| 6-1 | .3 | 0.17 | 200 | 190/59 | 0.62 |

The lower molecular weight PEO results in lower extruder pressure compared to the POLYOX 205.

EXAMPLE 7

This example illustrates the formation of a coating of the novel graft copolymer on silicone rubber.

A modified poly(ethylene oxide) was produced from poly(ethylene oxide) (Polyox WSR-205 resin, available from Union Carbide) grafted with 3% by weight of methacryloxypropyl trimethoxy silane (Dow Coming Z-6030 Silane, available from the Dow Coming Co.) in the presence of a peroxide initiator (Varox DBPH, supplied by R.T. Vanderbilt Co., Inc.) as described in Examples 1–6, above. A 2% by weight solution of this material was prepared by the addition of the dry copolymer to a suitable amount of water with stirring at room temperature. A portion of the solution was poured into a silicone rubber mold having a rectangular depression 2 mm deep. The solution was dried overnight at room temperature to provide a smooth film that became lubricious when re-wetted. The film adhered tenaciously to the surface of the silicone rubber.

EXAMPLE 8

This example illustrates the formation of a lubricious, absorbent coating on several different fibers and fabrics.

A modified poly(ethylene oxide) was produced from poly(ethylene oxide) (Polyox N-80 resin, available from Union Carbide) grafted with 6% by weight of methacryloxypropyl trimethoxy silane (Dow Corning Z-6030 Silane, available from the Dow Corning Co.) in the presence of a peroxide initiator (Varox DBPH, supplied by R.T. Vanderbilt Co., Inc.) as described in Examples 1–6, above. A 3% by weight solution of this material was prepared by the addition of the dry copolymer to a suitable amount of water with stirring at high shear using an Ultra Turrax mixer (available from IKA Laboratory Technology with offices in Wilmington, N.C.) at room temperature. This solution was used to saturate the following fabrics: (1) 0.45 ounces per square yard (osy) wettable spunbond diaper liner (available from Kimberly-Clark Corporation, Neenah, Wis.), (2) rayon bonded carded web (composed of 50% rayon and 50% polypropylene/polyethylene bicomponent binder fiber (BCW) (available from Kimberly-Clark Corporation, Neenah, Wis.), and (3) poly(lactic acid) (PLA) fiber surge material (available from Kimberly-Clark Corporation, Neenah, Wis.). The coated substrates were dried at 50° C. overnight. The weight percent of coating that was deposited upon each of the dried materials was determined, and each material was tested for saline uptake under 0.5 psi load (as described in the General Procedures, above). The results are shown in Table 11.

TABLE 11

Weight percent coating and amount of saline uptake for fabrics coated with 3% graft copolymer.

| SUBSTRATE | WEIGHT PERCENT COATING | SALINE UPTAKE AT 0.5 psi load (g/g) |
|---|---|---|
| 0.45 OSY Wettable Spunbond | 51% | 4.2 |
| Rayon BCW | 30% | 4.8 |
| PLA Surge Material | 32% | 10.8 |

The results illustrate that relatively inexpensive, readily available substrates can be coated with cross-linked modified poly(ethylene oxide) copolymer to form a hydrogel coating that is very absorbent in an aqueous fluid.

EXAMPLE 9

This example illustrates the formation of a lubricious, absorbent coating on PLA surge material.

A modified poly(ethylene oxide) was produced from poly(ethylene oxide) (Polyox N-80 resin, available from Union Carbide) grafted with 6% by weight of methacryloxypropyl trimethoxy silane (Dow Corning Z-6030 Silane, available from the Dow Corning Co.) in the presence of a peroxide initiator (Varox DBPH, supplied by R.T. Vanderbilt Co., Inc.) as described in Examples 1–6, above. A 7% by weight solution of this material was prepared by the addition of 28 g of the dry copolymer to 372 g of water with stirring at 11,000 rpm for 30 minutes using an Ultra Turrax mixer (available from IKA Laboratory Technology) at room temperature. This solution was placed in a dish on a sample of surge material (P-6951-82-1) made from PLA staple fiber. Pressure was applied to force the viscous solution into the surge structure. Excess solution was wrung out and the sample was dried for four hours at 50° C. The coating increased the weight of the fabric by an average of 62%. The coated surge sample quickly absorbed saline solution and retained 8.6 g/g of saline under 0.5 psi load.

EXAMPLE 10

This illustrates the efficacy of various fabrics coated with the novel absorbent poly(ethylene oxide) co-polymer for absorption of saline solution and wound fluid.

Several different substrate materials were coated with a copolymer produced from POLYOX N80 with 6% by weight engrafted Z6030 monomer by the method described in Examples 7 and 8, above. Table 12 shows the substrates that were coated and the weight percent of the dry copolymer coating that was retained on the fabric. Each of the coated materials was then tested for uptake of 0.9% saline retained under 0.5 psi weight, as described in the General Procedures, and for the absorption of wound fluid by the fluid handling capacity test for wound dressings. This test is described in the British Pharmacopoeia 1993, Addendum 1996, available from the British Pharmacopoeia Commission, London, UK. The simulated wound fluid used for this test consists of sodium chloride and calcium chloride solution containing 142 mmol of sodium ions and 2.5 mmol of calcium ions as the chloride salts. This solution has an ionic composition comparable to human serum or wound exudate. It is prepared by dissolving 8.298 g of sodium chloride and 0.368 g of calcium chloride dihydrate in deionized water and making up to 1 liter in a volumetric flask.

TABLE 12

Efficacy of various fabrics coated with the novel cross-linked modified poly(ethylene oxide) co-polymer for the absorption of saline solution and wound fluid.

| COATED SUBSTRATE | WEIGHT PERCENT COATING | FLUID HANDLING CAPACITY | | |
|---|---|---|---|---|
| | | UPTAKE OF 0.9% SALINE AT 0.5 psi (g/g) | WOUND FLUID ABSORBED (g/g) | TOTAL WOUND FLUID HANDLED PER 100 cm$^2$ OF DRESSING (g) |
| PLA BCW Surge | 32% | 10.8 | 18.6 | 33 |
| Polypropylene BCW Surge | 45% | 16.7 | 19.8 | 38 |
| Rayon BCW | 30% | 4.8 | 13 | 14 |
| Spunbond polypropylene 0.45 osy | 50% | 4.2 | 6.4 | 10 |

TABLE 12-continued

Efficacy of various fabrics coated with the novel cross-linked modified poly(ethylene oxide) co-polymer for the absorption of saline solution and wound fluid.

| COATED SUBSTRATE | WEIGHT PERCENT COATING | FLUID HANDLING CAPACITY | | |
|---|---|---|---|---|
| | | UPTAKE OF 0.9% SALINE AT 0.5 psi (g/g) | WOUND FLUID ABSORBED (g/g) | TOTAL WOUND FLUID HANDLED PER 100 cm$^2$ OF DRESSING (g) |
| SigmaDress hydrocolloid dressing | | | | 16 |
| ConvaTech Duoderm Hydrocolloid Dressing | | | | 15 |
| Dow Hickam Flexderm Hydrogel Dressing | | | | 24 |

These results indicate that fabrics coated with the novel cross-linked modified poly(ethylene oxide) co-polymer have equivalent or greater absorbent capacity as commercially available hydrocolloid wound dressings along with much greater mechanical integrity in the saturated condition. The commercial products in the table above were tested with the same method. A measure of g/g wound fluid absorbed is not included because these products have integral cover materials that cannot be removed without damaging the dressing. Therefore an accurate weight of the actual absorbent portion was not obtained. If the cover weight is included the g/g absorbency for all these products is less than 2 g/g.

EXAMPLE 11

This illustrates the preparation of a lubricious coating from an organic solvent. A modified poly(ethylene oxide) was produced from poly(ethylene oxide) (Polyox N-80 resin, available from Union Carbide) grafted with 6% by weight of methacryloxypropyl trimethoxy silane (Dow Corning Z-6030 Silane, available from the Dow Corning Co.) in the presence of a peroxide initiator (Varox DBPH, supplied by R.T. Vanderbilt Co., Inc.) as described in Examples 1–6, above. A 2% by weight solution of this material was prepared by the addition of 2 g of the dry copolymer to 98 g of acetonitrile with stirring at 11,000 rpm for 4 minutes using an Ultra Turrax mixer (available from IKA Laboratory Technology) at room temperature. 19.8 grams of this solution was combined with 28 grams of 2-butanone and 1 gram of water to provide a total resin concentration of 0.8%. A 9 cm sample of silicone rubber tubing (outer diameter 0.9 cm, inner diameter 0.6 cm, obtained from Ballard Medical) was dipped into the solution and dried at 50 C for 15 minutes. Two additional coatings were applied in the same manner, a total of three coating applications. The coated silicone tubing was non-tacky in the dry state. When the coated silicone tubing was immersed in water or 0.9% saline solution the coating became hydrated to provide a lubricious surface. Alternatively, the coating can imbibe water from body fluids, even if it is not exposed to water prior to introduction into the body. The coating retains its lubricating properties even after subsequent drying and rehydration.

EXAMPLE 12

This illustrates the controlled delivery of various therapeutic materials that were incorporated into the novel absorbent poly(ethylene oxide) co-polymer. A solution cast film was prepared by blending 2% (by weight) aqueous solutions in a 60:20:20 weight ratio of the following components: Polyox 205 (Union Carbide) with six weight percent of Dow Coming Z-6030 grafted thereonto; chitosan malate, and glycerin. The solution blend was poured into a polypropylene weighing dish. The water was evaporated at 50° C. for four hours to provide a thin, flexible, translucent film that contains at least 40% by weight water-soluble therapeutic materials. Similarly, a solution cast film was prepared by blending 2% (by weight) aqueous solutions of the following components: Polyox 205 (Union Carbide) with three weight percent of Dow Coming Z-6030 grafted thereonto with chitosan malate in a 60/40 weight ratio.

Alternatively, a film with therapeutic materials incorporated was prepared by "loading" a film in the following manner. A melt cast film was made of Polyox 205 (Union Carbide) with seven weight percent of Dow Coming Z-6030 grafted thereonto and then exposed to humid air to provide a cross-linked film with an absorbent capacity of approximately 9 grams per gram of dry film. A solution blend was prepared consisting of 97 grams of aloe vera solution (0.76% by weight) with 3 grams of glycerin. 24 grams of this solution blend was poured into a petri dish and the crosslinked film described above which weighed 2.66 grams in the dry state, was place into the solution blend. The film swelled and absorbed the solution within five minutes to produce a film gel that contained the aloe vera and glycerin. The swollen film gel was placed between two fiberglass screens and dried at 50° C. for four hours. The resultant dry film had an estimated composition of 75% grafted copolymer, 20% glycerin, and 5% aloe vera (a therapeutic agent beneficial for treating burns).

The coated polypropylene surge was prepared as describe in EXAMPLE 9. by blending 37.5 g 3% (by weight) aqueous solutions of Polyox 205 (Inion Carbide) with six weight percent of Dow Coming Z-6030 grafted thereonto; 1 gram of 30% glycerin solution and; and 9.9 gram of 1% aloe vera solution. This blend solution was placed in a dish on a sample of surge material made from polypropylene and polyester staple fiber. Pressure was applied to force the viscous solution into the surge structure. Excess solution was wrung out and the sample was dried for four hours at 50° C. The coating increased the weight of the fabric by 46 percent. A second coated surge material was made in exactly the same manner except a 3% (by weight) aqueous solutions of Polyox N80 (Union Carbide) with six weight percent of Dow Coming Z-6030 grafted thereonto was used. The coating increased the weight of the fabric by 44 percent.

To test the capability of the novel absorbent poly(ethylene oxide) co-polymer to deliver various therapeutic materials that were incorporated into the structure, an extraction experiment was done in the following manner. Weighed samples of the film or coated substrate, with compositions indicated in Table 13, were immersed for 15 minutes in 200 g of 0.9% saline solution at 37° C. for 15 minutes. This condition was chosen to simulate exposure to excess body fluid at body temperature. The samples were dried overnight at 50° C. and reweighed to determine the amount of material released from the sample. The results indicated that as the composition swells and absorbs the simulated body fluid at least a portion of the water-soluble component is released from the film or coating.

As described above, the therapeutic compounds can be combined into a film or coating with the novel co-polymer by multiple methods. The advantage is that such therapeutic materials can be incorporated into a coating, and the coating will then act to release the material over an extended period of time when the coating is exposed to body fluid, for example wound exudate. The solubility of the therapeutic material, the loading level of the therapeutic material, and the rate of swelling of the novel co-polymer can control the rate and amount of the therapeutic material released. Methods known in the art for controlling release rate from hydrogels by controlling the rate of fluid intake by means of blending or coating the surface are also anticipated.

TABLE 13

Delivery of therapeutic materials incorporated into films and coatings formed from the novel absorbent poly(ethylene oxide) co-polymer.

| MATERIAL | COMPOSITION[a] | THERAPEUTIC MATERIAL RELEASED (wt. %) | THERAPEUTIC MATERIAL REMAINING (wt. %) |
|---|---|---|---|
| Solution cast film | 60/20/20: 205-6 Copolymer/ Glycerin/Chitosan malate | 64% | 36% |
| Solution cast film | 60/40205-3 Copolymer/Chitosan | 100% | 0% |
| Loaded Film | 75/20/5: 205-7 Copolymer/ Glycerol/Aloe vera | 77% | 23% |
| Coated Polypropylene Surge | 75/20/5: 205-6 Copolymer/ Glycerol/Aloe vera | 45% | 55% |
| Coated Polypropylene Surge | 80/20/5: N80-6 Copolymer/ Glycerol/Aloe vera | 55% | 45% |

Notes:
[a]Numbers such as 60/20/20 give the parts by weight of the listed components in the cross-linked hydrogel. The designation 205-3 and 205-6 mean that the poly(ethylene oxide) resin that was used in the synthesis of the absorbent co-polymer was Polyox 205 (Union Carbide) and the weight percent of Dow Corning Z-6030 grafted thereonto was, respectively, 3% by weight, or 6% by weight, based on the poly(ethylene oxide). The designation N80-6 means that the poly(ethylene oxide) that was use in the synthesis of the absorbent co-polymer was Polyox N-80 (Union Carbide), and the weight percent of Dow Corning Z-6030 grafted thereonto was 6% by weight, based on the poly(ethylene oxide).

All references cited in this specification, including without limitation all papers, publications, patents, patent applications, presentations, texts, reports, manuscripts, brochures, books, internet postings, journal articles, periodicals, and the like, are hereby incorporated by reference into this specification in their entirety. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description shall be interpreted as illustrative and not in a limiting sense. These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A method of forming a coating on an article, the method comprising contacting the article with a copolymer comprising a water soluble base polymer having graft polymerized thereto in a non-terminal position an organic moiety that includes a group that reacts with water to form a silanol group; and curing the copolymer to form a coating comprising the crosslinked copolymer on the article.

2. The method according to claim 1, where the group that reacts with water to form a silanol group is a trialkoxy silane functional group.

3. The method according to claim 1, wherein said contacting comprises applying a film containing un-crosslinked copolymer to the article.

4. The method according to claim 3, wherein said applying is carried out under substantially water-free conditions.

5. The method according to claim 4, wherein the film substantially covers the exterior surface of the article.

6. The method according to claim 5, wherein the curing step comprises contacting the film with water.

7. The method according to claim 1, wherein the contacting step comprises forming a solution of the copolymer in a solvent and placing a film of solution on the article.

8. The method according to claim 7, wherein the solvent is water, an organic solvent, or a mixture thereof.

9. The method according to claim 8, wherein the solvent is water.

10. The method according to claim 7, wherein placing a film of solution on the article comprises dipping, spraying, printing, painting, or immersing the article with or in the solution.

11. The method according to claim 10, wherein curing the copolymer to form a coating of the cross-linked copolymer comprises removing solvent from the copolymer.

12. The method according to claim 11, wherein removing solvent from the copolymer comprises evaporating the solvent.

13. The method according to claim 12, wherein the evaporation comprises drying.

14. A coating on an article, the coating comprising a crosslinked hydrogel that includes a copolymer comprising water soluble base polymers having graft polymerized thereto organic moieties that react with water to form a silanol group, the copolymer being crosslinked through the silanol groups of the organic moieties to form a coating that is absorbent, lubricious and substantially non-water soluble.

15. The coating according to claim 14, wherein the copolymer comprises the organic moieties in an amount that is within a range of about 0.5 to about 10 percent by weight of the water soluble base polymer.

16. The coating according to claim 15, wherein the coating is transparent.

17. The coating according to claim 16, wherein the coating is resistant to fogging.

18. The coating according to claim 14, wherein the coating is anti-thrombogenic.

19. The coating according to claim 15, wherein the coating comprises, in addition, a releasable component.

20. The coating according to claim 19, wherein the releasable component is selected from the group consisting of therapeutic agents, bioactive agents, antibiotics, bactericides, fungicides, drugs, growth factors, peptides, proteins, enzymes, emollients, antiseptics, anti-oxidants, wetting agents, and mixtures thereof.

21. A coated article comprising an article coated with a crosslinked hydrogel that includes a copolymer comprising water soluble base polymers having graft polymerized thereto organic moieties that react with water to form a silanol group, the copolymer being crosslinked through the silanol groups of the organic moieties to form a coating that is absorbent, lubricious and substantially non-water soluble.

22. The coated article according to claim 21, wherein the article comprises metal, glass, natural or synthetic polymer, natural fiber, wood, another coating or paint, or a mixture thereof.

23. The coated article according to claim 22, wherein the coated article is a transparent lens or window.

24. The coated article according to claim 22, wherein the coated article is the water-contacting surface of a pipe, tube, pipeline, boat hull, submarine, torpedo, fishing line, fishing lure, water ski, or propeller.

25. The coated article according to claim 22, wherein the coated article is selected from the group consisting of medical instruments, bandages, drapes, fabrics, fibers, foams, films, tubing, catheters, shunts, artificial organs, dialysis apparatus, surgical instruments, stents, indwelling splints, and guide wires.

26. The coated article according to claim 25, wherein the coated article is a fiber comprising poly(propylene), poly (ethylene terephthalate), poly(lactic acid), or rayon.

27. The coated article according to claim 25, wherein the article is a woven or nonwoven fabric.

28. The coated article according to claim 25, wherein the coated article is a bandage, drape, diaper, feminine hygiene product, or an incontinence aid.

29. A coating solution comprising a mixture of a solvent and a copolymer comprising a water soluble base polymer having graft polymerized thereto in a non-terminal position an organic moiety that includes a group that reacts with water to form a silanol group.

30. The coating solution according to claim 29, wherein the water soluble base polymer is selected from the group consisting of poly(alkylene oxides), poly(ethylene oxide), poly(ethylene glycols), block copolymers of ethylene oxide and propylene oxide, poly(vinyl alcohol), poly(alkyl vinyl ethers), and mixtures thereof.

31. The coating solution according to claim 30, wherein the organic moiety is selected from the group consisting of methacryloxypropyl trimethoxy silane, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane.

32. The coating solution according to claim 30, wherein the group or a moiety that reacts with water to form a silanol group is an trialkoxy silane functional group.

33. The coating solution according to claim 32, wherein the trialkoxy silane functional group is one having the following structure:

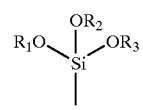

wherein $R_1$, $R_2$ and $R_3$ are alkyl groups independently having 1 to 6 carbon atoms.

* * * * *